United States Patent [19]

Agano

[11] Patent Number: 5,231,574
[45] Date of Patent: Jul. 27, 1993

[54] METHOD FOR DETECTING ARTIFACT SIGNAL COMPONENTS

[75] Inventor: Toshitaka Agano, Kanagawa, Japan

[73] Assignee: Fuji Photo Film Co., Ltd., Kanagawa, Japan

[21] Appl. No.: 504,164

[22] Filed: Apr. 3, 1990

[30] Foreign Application Priority Data

Apr. 6, 1989 [JP] Japan ................. 1-87709

[51] Int. Cl.⁵ .............. G06F 15/00; G06K 9/00; H04N 9/12
[52] U.S. Cl. ................. 364/413.13; 382/6; 358/56
[58] Field of Search .......... 364/413.13; 250/327.2; 382/54, 6, 26; 358/56

[56] References Cited

U.S. PATENT DOCUMENTS

| 4,258,264 | 3/1981 | Kotera et al. | 250/484.1 |
| 4,276,473 | 6/1981 | Kato et al. | 250/327.2 |
| 4,315,318 | 2/1982 | Kato et al. | 250/337 |
| 4,387,428 | 6/1983 | Ishida et al. | 364/413.13 |
| 4,703,537 | 11/1987 | Yamamoto et al. | 15/102 |
| 4,747,156 | 5/1988 | Wahl | 382/54 |
| 4,933,775 | 6/1990 | Shimura | 358/456 |
| 4,992,663 | 2/1991 | Takeo | 364/413.13 |

FOREIGN PATENT DOCUMENTS 56-11395 2/1981 Japan .
61-5193 2/1986 Japan .

Primary Examiner—Roy N. Envall, Jr.
Assistant Examiner—Frantzy Poinvil
Attorney, Agent, or Firm—Sughrue, Mion, Zinn, Macpeak & Seas

[57] ABSTRACT

A method for detecting artifact signal components comprises the steps of detecting an image signal made up of a series of image signal components representing a radiation image from a recording medium on which the radiation image has been recorded. Specific image signal components, which have values smaller than a predetermined threshold value, are detected from the image signal. Investigation is made to find how many neighboring picture elements the specific image signal components correspond to. In cases where the number of the neighboring picture elements is smaller than a predetermined number, it is determined that the specific image signal components are artifact signal components.

7 Claims, 1 Drawing Sheet

METHOD FOR DETECTING ARTIFACT SIGNAL COMPONENTS

BACKGROUND OF THE INVENTION

1. Field of the Invention

This invention relates to a method for detecting image signal components, which represent an artifact due to dust, a scratch, or the like on a radiation image recording medium, from an image signal made up of a series of image signal components obtained during an image read-out operation carried out on the recording medium, such as a stimulable phosphor sheet or X-ray film, on which a radiation image has been recorded.

2. Description of the Prior Art

Techniques for reading out a radiation image, which is recorded on a recording medium, in order to obtain an image signal, carrying out appropriate image processing on the image signal, and then reproducing a visible image by use of the processed image signal have heretofore been known in various fields.

For example, as disclosed in Japanese Patent Publication No. 61(1986)-5193, an X-ray image is recorded on a sheet of X-ray film having a small gamma value chosen according to the type of image processing to be carried out, the X-ray image is read out from the X-ray film with a microphotometer, or the like, and converted into an electric signal, and the electric signal (image signal) is processed and then used for reproducing the X-ray image as a visible image on a copy photograph or the like. In this manner, a visible image having good image quality with high contrast, high sharpness, high graininess, or the like can be reproduced.

Also, when certain kinds of phosphors are exposed to radiation such as X-rays, α-rays, β-rays, γ-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor. As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a sheet provided with a layer of the stimulable phosphor (hereinafter referred to as a stimulable phosphor sheet) is first exposed to radiation which has passed through an object such as the human body in order to store a radiation image of the object thereon, and is then scanned with stimulating rays, such as a laser beam, which cause it to emit light in proportion to the amount of energy stored during exposure to the radiation. The light emitted by the stimulable phosphor sheet, upon stimulation thereof, is photoelectrically detected and converted into an electric image signal. The image signal is then used to reproduce the radiation image of the object as a visible image on a recording material such as photographic film, on a display device such as a cathode ray tube (CRT), or the like.

During the recording of a radiation image on a recording medium, such as a stimulable phosphor sheet or X-ray film, if dust clings to the surface of the recording medium, the dust will prevent radiation from impinging upon the recording medium. Therefore, when an image signal is detected from the recording medium, on which a radiation image has thus been recorded, during an image read-out operation, and a visible image is reproduced from the image signal, a white dot-like artifact will occur at part of the visible image, which part corresponds to the part of the recording medium at which the dust was present. Particularly, in the radiation image recording and reproducing systems using stimulable phosphor sheets, if dust clings to the surface of a stimulable phosphor sheet, on which a radiation image has been stored, during an image read-out operation, the dust will prevent stimulating-rays from impinging upon the stimulable phosphor sheet. Therefore, the part of the stimulable phosphor sheet at which the dust is present will not be substantially caused to emit light in proportion to the amount of energy stored thereon during its exposure to radiation. Accordingly, when a visible image is reproduced from the image signal obtained during the image read-out operation, a white dot-like artifact will occur at part of the visible image, which part corresponds to the part of the stimulable phosphor sheet at which the dust was present. Also, in the radiation image recording and reproducing systems using stimulable phosphor sheets, if the surface of a stimulable phosphor sheet has a scratch, a flaw, or the like, stimulating rays irradiated to the stimulable phosphor sheet during an image read-out operation will be scattered by the scratch, the flaw, or the like. As a result, a white dot-like artifact will occur at part of a visible image reproduced from an image signal obtained during the image read-out operation, which part corresponds to the part of the stimulable phosphor sheet at which the scratch, the flaw, or the like, is present.

In cases where reproduced radiation images are utilized in diagnoses of human bodies, or the like, white dot-like artifacts very adversely affect accurate and efficient diagnoses. For example, in the case of a radiation image of the mamma, or the like, calcium salts which have deposited in a tissue will appear in the form of a white dot in a reproduced visible image. Such an effect is utilized in detecting a cancer, or the like. Therefore, if a white dot caused to occur in a reproduced visible image by the deposition of calcium salts (i.e. calcification) and a white dot-like artifact due to dust, a scratch, or the like, are discriminated from each other, a diagnosis cannot be carried out accurately. Of course, the size of a white dot-like artifact due to dust, a scratch, or the like, varies in accordance with the size of the dust, the scratch, or the like. It often occurs that the size of a white dot-like artifact is approximately equal to the size of a white dot caused to occur by calcification.

In order to eliminate the problems described above, various processes for preventing dust from clinging to recording media and preventing recording media from being scratched or flawed have heretofore been employed. For example, U.S. Pat. No. 4,703,537 discloses a method wherein dust is removed from a stimulable phosphor sheet by a cleaning roller.

However, considerable labor is required and it is actually difficult completely to prevent dust from clinging to recording media and to prevent recording media from being scratched or flawed.

If image signal components representing a white dot-like artifact due to dust, a scratch, or the like on a recording medium can be detected accurately from an image signal made up of a series of image signal components obtained during an image read-out operation carried out on the recording medium, such as a stimulable phosphor sheet or X-ray film, on which a radiation image has been recorded, it would become possible to prevent an artifact from occurring in a visible image reproduced from the image signal by carrying out an appropriate processing on the image signal components representing the artifact.

SUMMARY OF THE INVENTION

The primary object of the present invention is to provide a method for detecting artifact signal components, with which the image signal components representing a white dot-like artifact due to dust, a scratch, or the like on a recording medium are detected accurately from an image signal made up of a series of image signal components obtained during an image read-out operation carried out on the recording medium, such as a stimulable phosphor sheet or X-ray film, on which a radiation image has been recorded.

Another object of the present invention is to provide a method for detecting artifact signal components, which enables a visible radiation image having such good image quality to be reproduced that the visible image is effective as a tool in, particularly, the accurate and efficient diagnosis of an illness.

The present invention provides a method for detecting artifact signal components, which comprises the steps of:

i) detecting an image signal made up of a series of image signal components representing a radiation image from a recording medium on which the radiation image has been recorded, ii) detecting specific image signal components, which have values smaller than a predetermined threshold value, from said image signal, iii) finding how many neighboring picture elements said specific image signal components correspond to, and iv) in cases where the number of said neighboring picture elements is smaller than a predetermined number, determining that said specific image signal components are artifact signal components.

As described above, it often occurs that the size of a white dot caused to occur by calcification and the size of a white dot-like artifact due to dust, a scratch, or the like, are approximately equal to each other. The inventor carried out study and found that, in general, values of image signal components representing a white dot caused to occur by calcification and values of image signal components representing a white dot-like artifact due to dust, a scratch, or the like, are markedly different from each other. Specifically, in the case of an ordinary radiation image, values of image signal components representing a white dot caused to occur by calcification are, of course, smaller than the values of image signal components representing the part surrounding the white dot. Values of image signal components representing a white dot-like artifact due to dust, a scratch, or the like, are markedly smaller than the values of image signal components representing a white dot caused to occur by calcification. Therefore, specific image signal components, which have values smaller than a predetermined threshold value, can be regarded as at least being prospective artifact signal components.

A radiation image often includes an image of an extraneous material, such as a character formed of lead, an artificial organ, or a plaster cast, together with an object image. Values of image signal components representing such an extraneous material are also very small like the values of artifact signal components. However, the size of an image of such an extraneous material is distinctly larger than the size of a white dot due to dust, a scratch, or the like, which is present on a recording medium. Therefore, when the specific image signal components which correspond to neighboring picture elements fewer than a predetermined number are found, it is possible to discriminate the specific image signal components representing a white dot due to dust, a scratch, or the like, from the specific image signal components representing an extraneous material, such as a character formed of lead, an artificial organ, or a plaster cast.

As described above, with the method for detecting artifact signal components in accordance with the present invention, the image signal components representing a white dot-like artifact due to dust, a scratch, or the like on a recording medium can be detected accurately from an image signal made up of a series of image signal components obtained during an image read-out operation carried out on the recording medium, on which a radiation image has been recorded. Therefore, when the method for detecting artifact signal components in accordance with the present invention is used in combination with a simple image processing method, an artifact which resembles an image of a calcified part of an object can be prevented from occurring in a reproduced visible image. Accordingly, it becomes possible to reproduce a visible radiation image having such good image quality that the visible image is effective as a tool in, particularly, the accurate and efficient diagnosis of an illness.

DESCRIPTION OF THE PREFERRED EMBODIMENTS

The present invention will hereinbelow be described in further detail with reference to the accompanying drawings.

Figure 1:
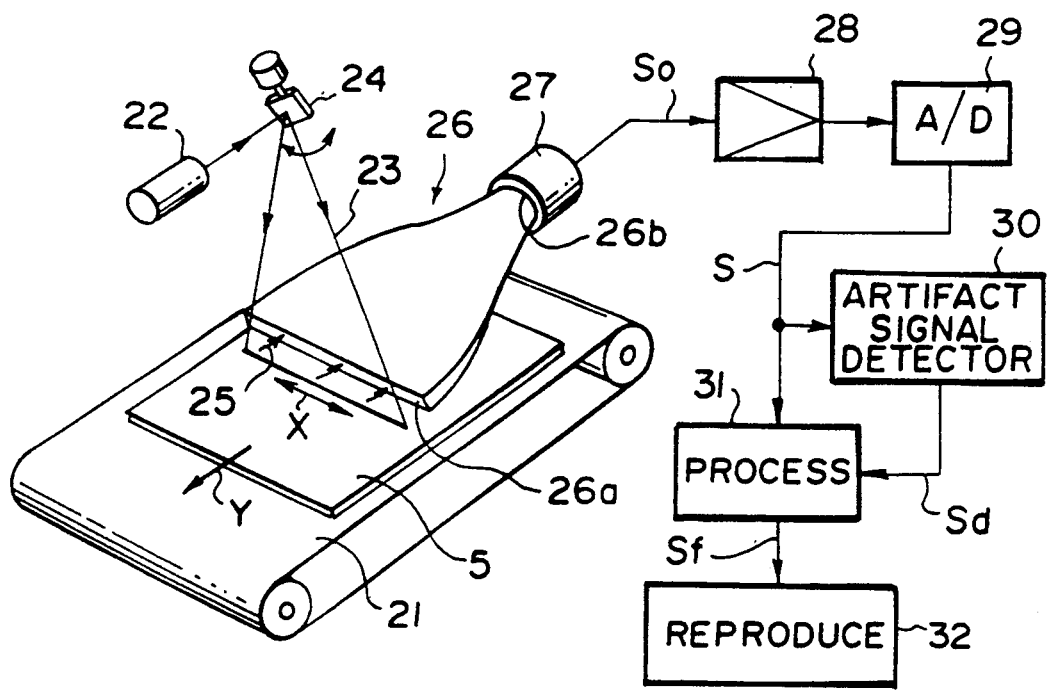
FIG. 1 is a schematic view showing an example of the radiation image read-out and reproducing system wherein an embodiment of the method for detecting artifact signal components in accordance with the present invention is employed.

With reference to FIG. 1, a stimulable phosphor sheet 5 has already been exposed to radiation, which has passed through an object, in order to store a radiation image thereon. The stimulable phosphor sheet 5, on which the radiation image has been stored, is conveyed in a sub-scanning direction indicated by the arrow Y by a sheet conveyance means 21. The sheet conveyance means 21 may be constituted of an endless belt or the like. A laser beam 23 which serves as stimulating rays is produced by a laser beam source 22. The laser beam 23 is deflected by a light deflector 24, such as a galvanometer mirror, and is caused to scans the stimulable phosphor sheet 5 in main scanning directions indicated by the double headed arrow X, which directions are approximately normal to the sub-scanning direction indicated by the arrow Y. When the stimulable phosphor sheet 5 is exposed to the laser beam 23, the exposed portion of the stimulable phosphor sheet 5 emits light 25 in an amount proportional to the amount of energy stored thereon during its exposure to radiation. The emitted light 25 is guided by a light guide member 26 and photoelectrically detected by a photomultiplier 27, which serves as a photodetector.

The light guide member 26 is formed of a light guiding material such as an acrylic plate and has a linear light input face 26a, positioned so that it extends along the main scanning line on the stimulable phosphor sheet 5, and a ring-shaped light output face 26b, positioned so that it is in close contact with a light receiving face of the photomultiplier 27. The emitted light 25, which has entered the light guide member 26 at its light input face 26a, is guided through repeated total reflection inside of the light guide member 26, emanates from the light output face 26b, and is received by the photomultiplier 27. In this manner, the amount of the emitted light 25, which amount represents the radiation image, is converted into an electric signal by the photomultiplier 27.

Figure 2:
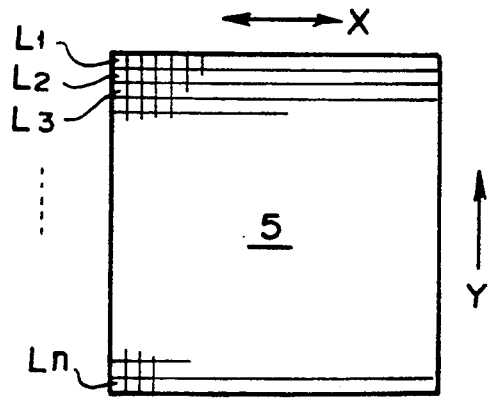
FIG. 2 is an explanatory view showing how image signal components corresponding to every row of an array of picture elements are sampled.
Figure 3:
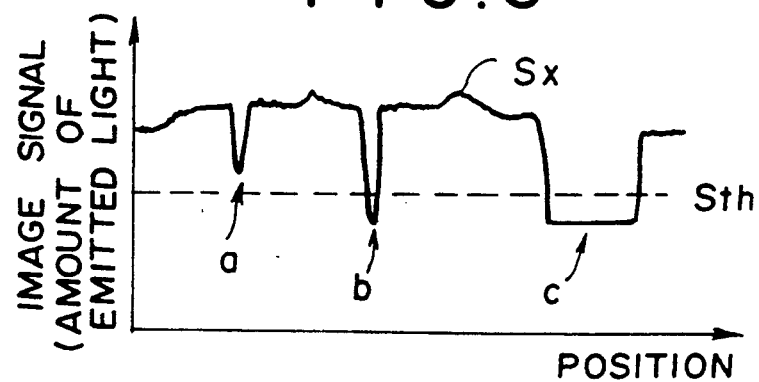
FIG. 3 is an explanatory graph showing how specific image signal components are detected with an embodiment of the method for detecting artifact signal components in accordance with the present invention.

An output signal So generated by the photomultiplier 27 is logarithmically amplified by a logarithmic amplifier 28, and digitized by an A/D converter 29 into a read-out image signal S. The digital read-out image signal S is fed into an artifact signal detecting apparatus 30 and an image processing apparatus 31. How the artifact signal detecting apparatus 30 detects artifact signal components will be described hereinbelow. By way of example, as shown in FIG. 2, the artifact signal detecting apparatus 30 samples image signal components S1 corresponding to a row L1 of an array of picture elements, which row extends along the main scanning directions indicated by the double headed arrow X, from the read-out image signal S. Also, the artifact signal detecting apparatus 30 samples image signal components S2, S3, ..., Sn, which respectively correspond to rows L2, L3, ..., Ln of the array of picture elements, from the read-out image signal S. Thereafter, the artifact signal detecting apparatus 30 finds the distribution of the values of the image signal components corresponding to each row of the array of picture elements. By way of example, the values of the image signal components corresponding to each row of the array of picture elements are distributed as shown in FIG. 3. In FIG. 3, part a represents the image signal components corresponding to a calcified part of the object. Part b represents the image signal components which have markedly small values and which correspond to the part of the stimulable phosphor sheet 5 where dust, a scratch, or the like is present. Part c represents the image signal components corresponding to the part at which a character formed of lead, an artificial organ, or the like, is present.

Thereafter, the artifact signal detecting apparatus 30 compares the values of the sampled image signal components Si (i=1, 2, 3, ..., n) with a predetermined threshold value Sth and finds image signal components having values smaller than the predetermined threshold value Sth. In general, the values of the image signal components (the part b), which correspond to the part of the stimulable phosphor sheet 5 where dust, a scratch, or the like is present, are markedly smaller than the values of the image signal components (the part a) corresponding to a calcified part of the object. Therefore, when the threshold value Sth is set to an appropriate value selected experimentally, only the image signal components represented by the part b can be detected as being specific image signal components, whereas the image signal components represented by the part a are not detected as being specific image signal components. The values of the image signal components represented by the part c are approximately equal to the values of the image signal components represented by the part b. Therefore, the image signal components represented by the part c are also detected as being the specific image signal components.

After detecting the specific image signal components, the artifact signal detecting apparatus 30 finds how many neighboring picture elements the specific image signal components correspond to. In cases where the number of the found neighboring picture elements is smaller than a predetermined number, for example, smaller than 10, it is determined that these specific image signal components are artifact signal components. In this embodiment, the size of each picture element is equal to 200 $\mu$m $\times$ 200 $\mu$m. Therefore, a group of 10 picture elements corresponds to a 2 mm length of the stimulable phosphor sheet 5. In general, the size of dust, a scratch, or the like on the stimulable phosphor sheet 5 is approximately 1 mm $\times$ 1 mm and is at most smaller than 2 mm. On the other hand, the size of a character formed of lead, or the like, is ordinarily larger than 10 mm $\times$ 10 mm. Accordingly, only the specific image signal components represented by the part b in FIG. 3 are detected as being artifact signal components, while the specific image signal components represented by the part c are not detected as being artifact signal components.

The artifact signal detecting apparatus 30 carries out the aforesaid processing on each of the group of image signal components S1, the group of image signal components S2, the group of image signal components S3, ..., the group of image signal components Sn, and generates a picture element position signal Sd which represents the positions of the picture elements corresponding to the detected artifact signal components. The picture element position signal Sd is fed into the image processing apparatus 31 shown in FIG. 1. The image processing apparatus 31 converts the values of the image signal components of the read-out image signal S received from the A/D converter 29, which image signal components correspond to the positions of the picture elements represented by the picture element position signal Sd, into values corresponding to the maximum image density. The image processing apparatus 31 also carries out a gradation processing, a frequency response processing, or the like, on the read-out image signal S. An image signal Sf obtained from the processing is fed into an image reproducing apparatus 32. The image reproducing apparatus 32 is constituted of, for example, a light beam scanning recording apparatus with which a sheet of photosensitive film is scanned with a light beam, or an image displaying means such as a CRT device. The image reproducing apparatus 32 reproduces the radiation image represented by the image signal Sf, i.e. the radiation image which was stored on the stimulable phosphor sheet 5, as a visible image from the image signal Sf.

The artifact signal components represented by the part b in FIG. 3 have been processed by the image processing apparatus 31 in the manner described above. Therefore, the image information at the part of the stimulable phosphor sheet 5, at which the dust, the scratch, or the like was present, is reproduced as having the maximum image density (i.e. in black) in the visible image. Accordingly, the part of the visible image corresponding to said part of the stimulable phosphor sheet 5 can be clearly discriminated from a white dot caused to occur by calcification. Also, in the reproduced visible image, the image information at the part corresponding to a character formed of lead, an artificial organ, or the like is reproduced into an image density with which the image information will ordinarily be reproduced.

In the embodiment described above, the values of the artifact signal components are converted into the values representing the maximum image density. Alternatively, the values of the artifact signal components may be converted into the values of the image signal components corresponding to the picture elements which are present in the vicinity of the picture elements corresponding to the artifact signal components. In such cases, no adverse effect of the dust, the scratch, or the like appears in the reproduced visible image. Also, the threshold value Sth may be set as a relative value (a difference) with respect to the mean value of the values of the image signal components corresponding to the picture elements which are present in the vicinity of the picture elements corresponding to the artifact signal components.

Also, in the embodiment described above, during the discrimination of the image signal components corresponding to a character formed of lead, or the like, from the artifact signal components, the artifact signal detecting apparatus 30 counts the number of neighboring picture elements to which the specific image signal components correspond and which are adjacent to each other along each row of an array of picture elements. Alternatively, the artifact signal detecting apparatus 30 may count the number of neighboring picture elements to which the specific image signal components correspond and which are adjacent to each other along each column of an array of picture elements. As another alternative, the artifact signal detecting apparatus 30 may count the number of neighboring picture elements to which the specific image signal components correspond and which are adjacent to each other along a plurality of rows and columns of an array of picture elements, i.e. the number of the neighboring picture elements corresponding to the two-dimensional size of the part of the image, which part corresponds to the character formed of lead, the dust, or the like.

In the embodiment described above, a stimulable phosphor sheet is used as the radiation image recording medium. The method for detecting artifact signal components in accordance with the present invention is applicable also when an X-ray image is read out from the conventional silver halide photographic film.

I claim:
1. A method for detecting artifact signal components, which comprises the steps of:
   i) detecting an image signal made up of a series of image signal components representing a radiation image from a recording medium on which the radiation image has been recorded,
   ii) sampling said image signal components to determine values of said image signal components,
   iii) comparing said values of said image signal components directly with a predetermined threshold value,
   iv) detecting specific image signal components based upon said comparison, where said values of said specific image signal components are smaller than said predetermined threshold value,
   v) for each of said specific image signal components evaluating all of the contiguous image signal components to determine which of said contiguous image signal components are specific image signal components;
   vi) determining for each of said specific image signal components the number of contiguous image signal components which have been detected as specific image signal components, and
   vii) in cases where the number of said contiguous image signal components determined to be specific image signal components is smaller than a predetermined number, determining that said specific image signal components are artifact signal components.

2. A method as defined in claim 1 wherein the number of said contiguous picture elements is counted along each row or column of an array of picture elements.

3. A method as defined in claim 1 wherein the number of said contiguous picture elements is counted along a plurality of rows and columns of an array of picture elements.

4. A method as defined in claim 1 wherein said recording medium is a stimulable phosphor sheet on which a radiation image has been stored.

5. A method as defined in claim 1 wherein said image signal is obtained from a read-out operation wherein said stimulable phosphor sheet is exposed to stimulating rays which cause said stimulable phosphor sheet to emit light in proportion to an amount of energy stored thereon during exposure to radiation, and the emitted light is detected photoelectrically.

6. A method as defined in claim 5 wherein said stimulating rays are a laser beam.

7. A method as defined in claim 1 wherein said recording medium is photographic film.

* * * * *